United States Patent [19]
Kato et al.

[11] Patent Number: 5,037,526
[45] Date of Patent: Aug. 6, 1991

[54] WATER-PROOF TYPE OXYGEN SENSOR

[75] Inventors: Nobuhide Kato; Masanori Katsu, both of Aichi, Japan

[73] Assignee: NGK Insulators, Ltd., Aichi, Japan

[21] Appl. No.: 517,697

[22] Filed: May 2, 1990

[30] Foreign Application Priority Data

May 15, 1989 [JP] Japan .............................. 1-55573[U]

[51] Int. Cl.$^5$ ......................................... G01N 27/407
[52] U.S. Cl. .................... 204/428; 204/426; 204/427; 204/429
[58] Field of Search ............ 204/427, 428, 429, 153.18

[56] References Cited

U.S. PATENT DOCUMENTS

| | | | |
|---|---|---|---|
| 4,123,131 | 10/1978 | Pearce et al. | 204/428 X |
| 4,717,464 | 1/1988 | Oshima et al. | 204/427 |
| 4,786,397 | 11/1988 | Barbieri et al. | 204/427 |
| 4,786,399 | 11/1988 | Wertheimer et al. | 204/427 |
| 4,818,364 | 4/1989 | Weber et al. | 204/427 |
| 4,883,643 | 11/1989 | Nishio et al. | 204/429 X |

Primary Examiner—T. Tung
Attorney, Agent, or Firm—Parkhurst, Wendel & Rossi

[57] ABSTRACT

A water-proof type oxygen sensor including a sensor element having inner and outer electrodes at inner and outer surfaces, respectively; a metallic cap for housing the sensor element; a gas-tight sealing member provided in the cap for isolating the exhaust gases from the air; communicating openings provided in the cap for communicating a space inside the cap with the air; and a communicating member arranged around the outer periphery of the communicating openings and having gas permeability and water-repellent property. The inner and outer electrodes are adapted to contact with air and exhaust gases. The communicating member is cylindrical and is fixed to the metallic cap through a metallic fixing member having a coefficient of thermal expansion almost equal to that of the metallic cap.

3 Claims, 4 Drawing Sheets

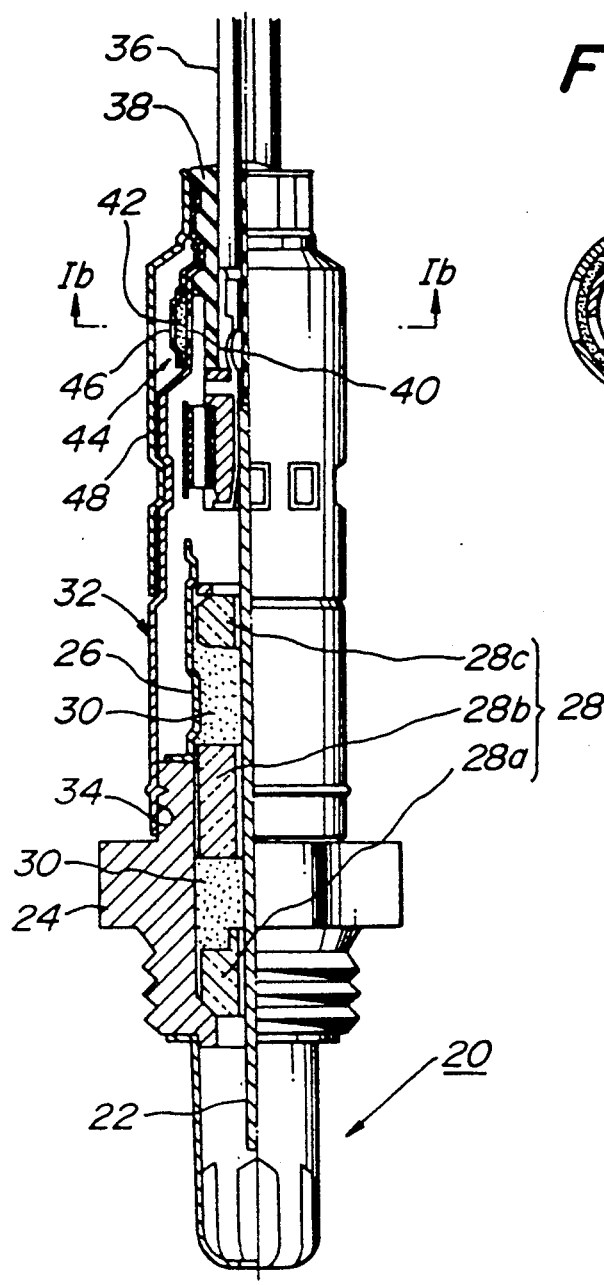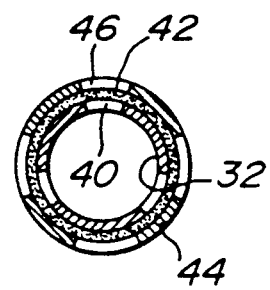
FIG_1a
FIG_1b

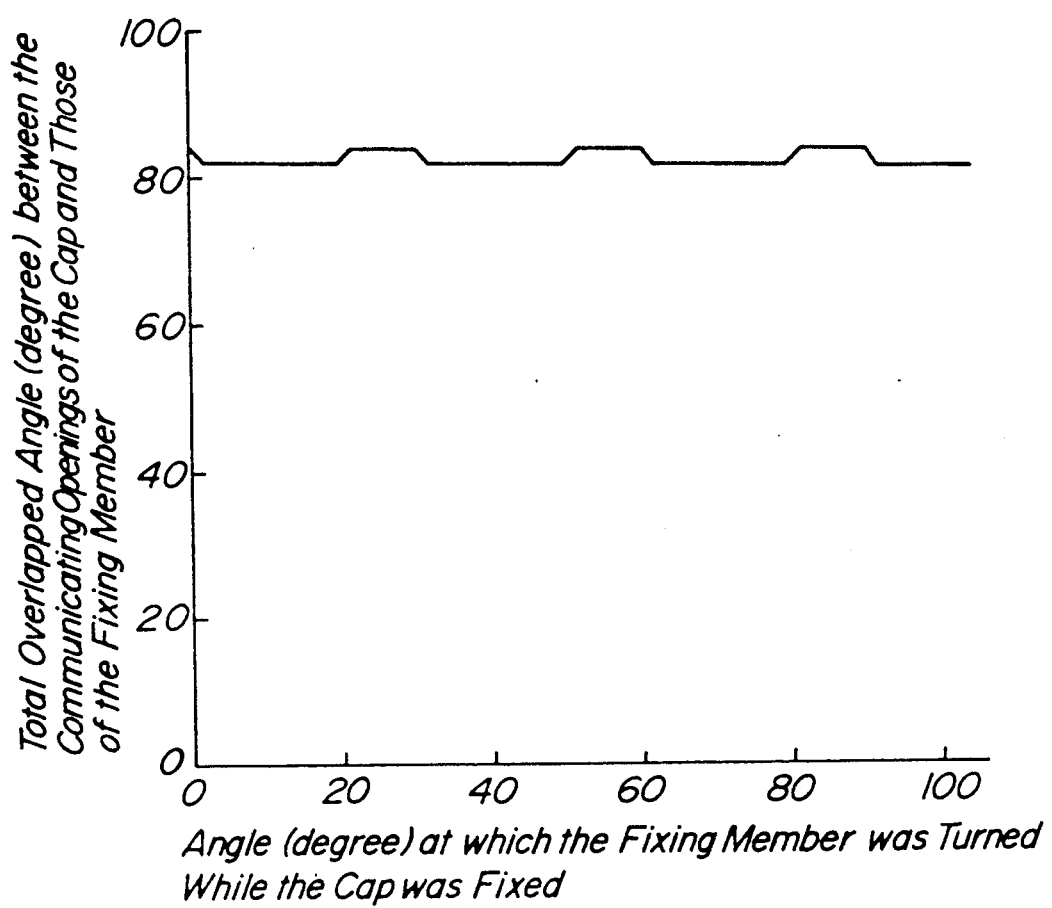
FIG_3

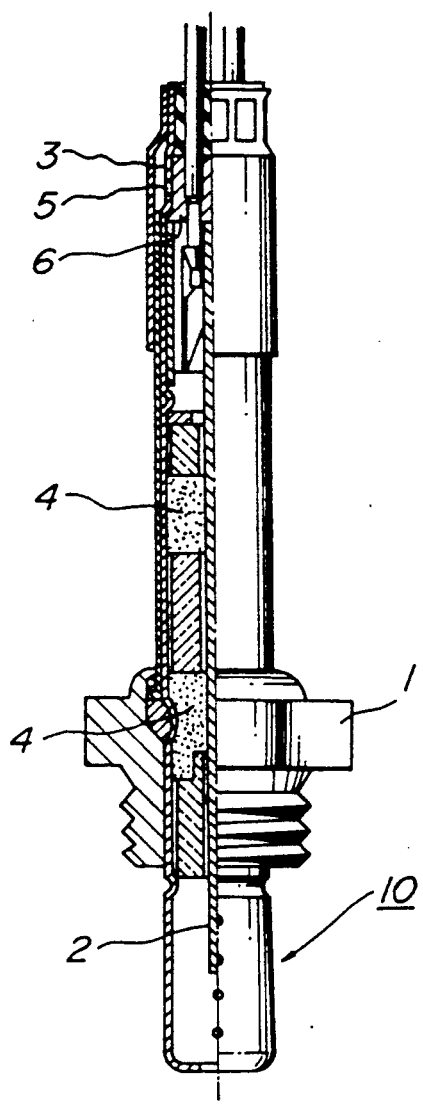
FIG_4
PRIOR ART

WATER-PROOF TYPE OXYGEN SENSOR

BACKGROUND OF THE INVENTION

1. Field of the Invention

The present invention relates to so-called water-proof type oxygen sensors each comprising a sensor element having inner and outer electrodes at inner and outer surfaces thereof, respectively, which inner and outer electrodes are to contact with surrounding air and exhaust gases, respectively; a metallic cap for housing the sensor element; a gas-tight sealing member arranged inside the cap for isolating the exhaust gases from the surrounding air, and a communicating member having a water-repelling property for communicating the surrounding air with the air inside the gas-tight sealing member.

2. Related Art Statement

Water-proof type oxygen sensors conventionally have been known as oxygen concentration detectors for exhaust gases from automobiles.

Since these oxygen sensors use surrounding air as a reference oxygen atmosphere, they are constructed to isolate the air as the reference oxygen atmosphere from the gases to be measured. In order to isolate air from the gases to be measured, in the case; of an oxygen sensor 10 as shown in FIG. 4, a gas-tight sealing member, for example, talc 4 is charged between a planar sensor element 2 placed in a metallic housing 1 and a metallic cap 3.

In this manner, an inner electrode is isolated from the gases to be measured, and an air introduction path is provided for introducing the surrounding air into the reference oxygen electrode.

As shown in FIG. 4, the air introduction path is constituted by communicating openings 5 provided in the metallic cap 3, and a column-like communicating member 6 arranged inside the metallic cap 3 and having gas permeability and water-repelling property, while the metallic cap 3 is caulked from the externally peripheral side to intimately adhere the inner surface of the metallic cap 3 with the peripheral surface of the communicating member 6. By this construction, air can be fed to the reference oxygen electrode, while the water-proof structure is maintained.

However, when the water-proof type oxygen sensor having such a construction is repeatedly heated at high temperatures and cooled during use for a long time period, a gap is formed between the metallic cap 3 and the communicating member 6 (generally made of a resinous material) due to difference in thermal expansion between them.

SUMMARY OF THE INVENTION

It is therefore an object of the present invention to solve the above-mentioned problem, and to provide a water-proof type oxygen sensor which does not encounter degradation of its water-proof property even during use for a long period.

The water-proof type oxygen sensor according to the present invention comprises a sensor element having inner and outer electrodes at inner and outer surfaces, respectively, which inner and outer electrodes are adapted to contact with surrounding air and exhaust gases, respectively; a metallic cap for housing the sensor element, a gas-tight sealing member provided in the cap for isolating the exhaust gases from the air; communicating openings provided in the cap for communicating a space inside the cap with the air, and a communicating member arranged around the outer periphery of the communicating openings and having gas permeability and water-repellent property, wherein the communicating member is cylindrical and is fixed to the metallic cap through a metallic fixing member having a coefficient of thermal expansion almost equal to that of the metallic cap.

In the above construction, since the cylindrical communicating member is fixed to the metallic cap by the metallic fixing member having a coefficient of thermal expansion almost equal to that of the metallic cap, thermal expansion can be reduced by decreasing the volume of the communicating member, which volume contributes to the thermal expansion. The communicating member is held by the cap and the fixing member having almost the same coefficient of thermal expansion. As a result, the formation of a gap between the communicating member and the cap can be prevented, so that water or the like will not enter the interior of the oxygen sensor through such a gap.

When the communicating openings of each of the metallic cap and the metallic fixing member for fixing the communicating member are circumferentially equidistantly arranged while the number of the openings of the metallic cap is made different from that of the openings of the metallic fixing member, at least a part of the communicating openings of the former can be overlapped with those of the latter whenever the cap and the fixing member are arranged in any positional relationship. Thus, air communication can be acquired more excellently.

The water permeable rate of the communicating member is preferably not more than 2 cc/min under pressure of 0.5 kg/cm$^2$. When the permeable rate of the communicating member falls in the above range, sufficient water-repelling property required in the present invention can be obtained. On the other hand, the gas permeable rate of the communicating member is preferably not less than 1 cc/min under a pressure of 0.5 kg/cm$^2$, because, in this case, the gas permeability required in the present invention can be assured. Thus, it is preferable that the porosity and the thickness of the communicating member are set to satisfy that the water permeable rate of the communicating member is not more than 2 cc/min under pressure of 0.5 kg/cm$^2$ and the surface area of the communicating member is set that the gas permeable rate is not less than 1 cc/min under a pressure of 0.5 kg/cm$^2$.

These and other objects, features and advantages of the invention will be appreciated upon reading the following description of the invention taken in conjunction with the attached drawings, with the understanding that some modifications, variations, and changes of the same could be made by the skilled person in the art to which the invention pertains without departing from the spirit of the invention or the scope of claims appended hereto.

BRIEF DESCRIPTION OF THE ATTACHED DRAWINGS

For a better understanding of the invention, reference is made to the attached drawings, wherein:

FIG. 1a is a partial sectional view of a structural embodiment of the water-proof type oxygen sensor according to the present invention, and FIG. 1b is a partial sectional view of FIG. 1a taken along line Ib—Ib;

FIG. 3 is a graph showing an overlapped angle of communicating openings when a cap is fixed and a fixing member is turned; and FIG. 4 is a partially sectional view of an example of the conventional water-proof type oxygen sensor.

DETAILED DESCRIPTION OF THE INVENTION

Figure 2:
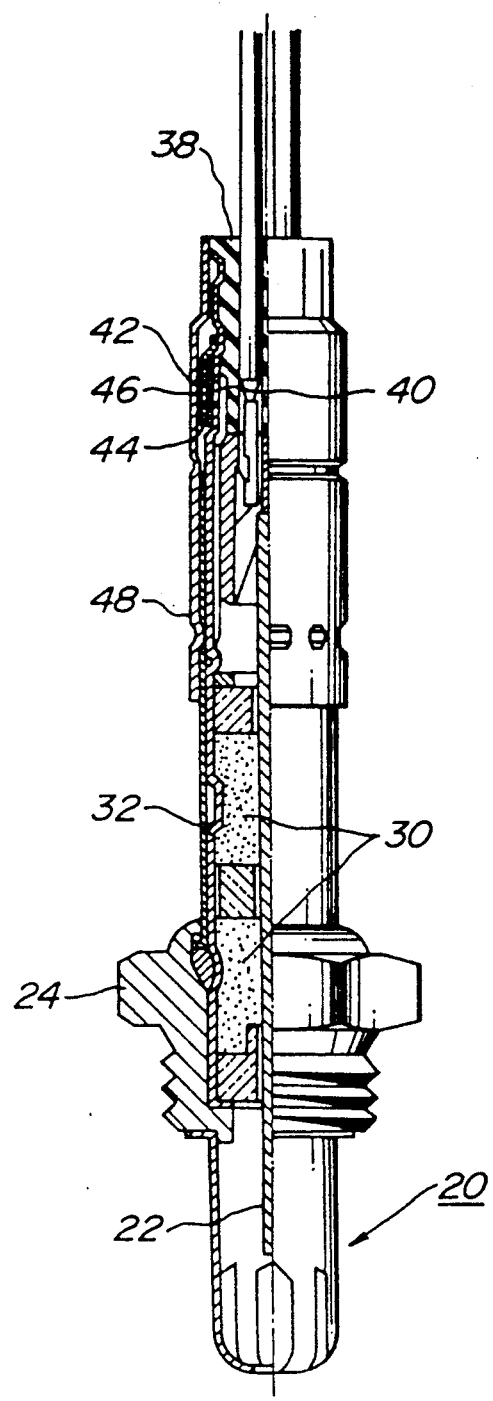
FIG. 2 is a partial sectional view of another structural embodiment of the water-proof type oxygen sensor according to the present invention.

FIGS. 1a and 1b are a partial sectional view and a sectional view along a line Ib—Ib of the structure of an embodiment of the present invention, respectively. In the oxygen sensor 20 according to the present invention shown in FIGS. 1a and 1b, a planar sensor element 22 is gas-tightly fixed and sealed to a metallic housing 24 and a metallic inner cylindrical tube 26 fixedly welded thereto, by means of talc 30 filled between ceramic supporters 28: 28a, 28b, 28c. Further, in order to protect the sensor element 22 from the exterior environment, a metallic cap 32 is fitted to the outer periphery of an upper annular projection 34 of the housing 24, and the former is gas-tightly fixed to the entire periphery of the latter by welding. On the other hand, a rubber plug 38 is sealingly fixed, through caulking the cap 32, to the cap at an upper end side opposite to the side on which the cap is fitted to the housing 24. Lead wires 36 are inserted through the rubber plug 38. The lead wires 36 are electrically connected to terminal electrodes of the sensor element 22.

Further, as shown in FIG. 1b, communicating openings 40 are bored in the outer peripheral wall of the cap 32 on the side of the upper open end to communicate with surrounding air. A cylindrical communicating member 42 is arranged around the outer periphery of the communicating openings 40, and a cylindrical metallic fixing member 44 is arranged around the outer side of the communicating member 42. Upper and lower end portions of the metallic fixing member 44 are caulked over its entire periphery to fix the inner communicating member 42. Communicating openings 46 are similarly bored in the peripheral wall of the metallic fixing member 44. A metal boot 48 is arranged to cover the metallic fixing member 44 for protecting the communicating member.

Next, the reason why water proofing is not damaged in the construction of the present invention will be explained below with reference to the conventional example in FIG. 4 and the embodiment of the present invention shown in FIG. 1. The water proofing is deteriorated by a gap occurring due to difference in thermal expansion between the communicating member (generally, a resinous material) and the metal during heat cycling (e.g. 300° C. ⟷ room temperature, 25° C.).

First, the gap occurring between the column-like communicating member 6 and the metallic cap 3 in FIG. 4 will be explained. As a matter of course, no gap is present between the communicating member 6 and the metallic cap 3 until the assembled oxygen sensor 10 is heated. Consider that the oxygen sensor 10 is heated (e.g. 300° C.). At that time, since the coefficient of thermal expansion of the communicating member 6 is greater than that of the metallic cap 3 (SUS 304), no gap is formed yet. However, since the communicating member 6 made of the resinous material has almost no elasticity, it is plastically deformed in the state that the communicating member is vertically expanded inside the metallic cap 3. Next, consider that the oxygen sensor is cooled to room temperature. At that time, since the coefficient of thermal expansion of the communicating member 6 is greater, a gap is formed between the metallic cap 3 and the communicating member 6.

For example, assume that the outer diameter of the communicating member, the coefficient of thermal expansion of the communicating member, and that of SUS 304 are 10 mm in diameter, $150 \times 10^{-6}/°C$., and $18 \times 10^{-6}/°C$. respectively, and the temperature is changed from 300° C. to 25° C. The amount of the gap may be calculated as follows:

$$\text{Amount of the gap} = (150 - 18) \times 10^{-6} \times (300 - 25) \times 10$$
$$= 0.36 \text{ mm}$$

If water is applied to the oxygen sensor 10, water enters the inside of the oxygen sensor through such a great gap. When this water evaporates, a reference oxygen partial pressure drops, thus lowering electromotive forces.

On the other hand, a gap is also formed among the cylindrical communicating member 42, the metallic cap 32 and the metallic fixing member 44 according to a similar mechanism in the case of the embodiment of the present invention shown in FIG. 1. However, since the communicating member 42 is sandwiched between the metallic members both having the same coefficient of thermal expansion and the thickness of the member 42 is, for example, as small as 0.3 mm, the gap amount is very small. For this reason, the gap amount is calculated below on the above assumption as mentioned above.

$$\text{Gap amount} = (150-18) \times 10^{-6} \times (300-25) \times 0.3 = 0.01 \text{ mm}$$

Thus, water cannot enter the inside of the oxygen sensor through such a small gap.

As is seen from the above explanation, the gist of the present invention is that invasion of water is interrupted by arranging the thin cylindrical communicating member 42 between the metallic cap 32 and the fixing member 44 both having almost the same coefficient of thermal expansion and by suppressing the amount of the gap formed. It is preferable to set the thickness of the communicating member at not more than 1 mm.

Since the coefficient of thermal expansion of the metallic cap 32 is made almost the same as that of the metallic fixing member 44, it is preferable that the material of the former is the same as that of the latter. However, different materials may be used for them in combination when a difference in the coefficient of thermal expansion is smaller between these materials as compared with that between the materials and the communicating member 42. For example, a combination of SUS 304 and SUS 430 ($18 \times 10^{-6}/°C$., $11 \times 10^{-6}/°C$.) may be employed.

In the invention embodiment of FIG. 1, the communicating openings 40 and 46 of the metallic cap 32 and the fixing member 44, respectively, are staggered with respect to the number and the location. That is, in this embodiment, the communicating openings 40 are provided in the cap 32 in tridivided fashion at a central angle 40°, while the communicating openings 46 having a central angle of 62° are formed in the fixing member 44 in a tetradivided fashion. By such a combination, as shown in FIG. 3, the area at which the openings 40 and 46 overlap can be made constant irrespective of their mutually positional relationship to assure stable ventilation degree.

FIG. 2 is a partial sectional view of another embodiment according to the present invention. In the embodiment shown in FIG. 2, the same reference numerals are given to the same or similar parts as those in FIG. 1, and their explanation is omitted. Where FIG. 2 differs from the embodiment of FIGS. 1a and 1b is that while in the embodiment of FIGS. 1a and 1b, the communicating member is fixed by caulking the upper and lower ends of the fixing member 44 over the entire periphery, in the embodiment of FIG. 2, the entire peripheral face of the fixing member is fixedly caulked to fix the communicating member 42.

In both of the embodiments, the rubber plug 38 is fixed to the upper end portion of the cap 32 by caulking at two stages, which can more firmly fix the rubber plug 38 and can prevent the formation of the gap between the cap and the rubber plug as compared with a one stage caulking. Thereby, the water-proofing property of the oxygen sensor is improved.

As mentioned above, since the oxygen sensor according to the present invention is constituted such that the surrounding air-communicating structure is attained while the cylindrical communicating member is sandwiched between the metallic cap and the metallic fixing member both having almost the same coefficient of thermal expansion, a gap can be prevented from being formed at the communicating portion due to the difference in thermal expansion. Thus, a water-proofing type oxygen sensor free from reduction in water proofness even during long periods of use can be obtained.

What is claimed is:

1. A water-proof oxygen sensor, comprising:
 a sensor element having a first electrode formed on a first surface thereof and a second electrode formed on a second surface thereof, said first electrode being in communication with air and said second electrode being in communication with exhaust gases;
 a metallic cap encompassing said sensor element, said metallic cap comprising communicating apertures formed therethrough for communicating an interior of said metallic cap with air;
 at least one gas-tight sealing member provided in said sensor for isolating said exhaust gases from said air;
 a communicating member arranged entirely around an outer periphery of said metallic cap so as to cover said communicating apertures in said metallic cap, said communicating member being gas permeable and water repellent; and
 a metallic fixing member arranged entirely around said communicating member, said metallic fixing member being crimped at upper and lower end portions thereof against said metallic cap such that said communicating member is entirely sealed between said metallic cap and said metallic fixing member, said metallic fixing member comprising communicating apertures formed therethrough for communicating said communicating member with air;
 wherein said metallic cap and said metallic fixing member have substantially equal thermal expansion coefficients.

2. The water-proof oxygen sensor of claim 1, further comprising a metallic boot arranged around said metallic fixing member and said metallic cap, wherein a lower end of said metallic boot is spaced from said metallic cap so as to provide communication between an interior of said metallic boot with air.

3. The water-proof oxygen sensor of claim 1, wherein the communicating apertures formed in each of said metallic cap and said metallic fixing member are spaced circumferentially equidistant, an the number and arrangement of said communicating apertures formed in said metallic cap are staggered from those formed in said metallic fixing member.

* * * * *